US009707256B2

(12) United States Patent
Soker et al.

(10) Patent No.: US 9,707,256 B2
(45) Date of Patent: Jul. 18, 2017

(54) METHODS OF MAKING ENDOTHELIAL SCAFFOLDS

(71) Applicant: Wake Forest University Health Sciences, Winston-Salem, NC (US)

(72) Inventors: Shay Soker, Greensboro, NC (US); J. Koudy Williams, Clemmons, NC (US); Patrick Laber, Winston-Salem, NC (US); Margaret Greven, Winston-Salem, NC (US); Keith A. Walter, Lewisville, NC (US)

(73) Assignee: Wake Forest Institute for Regenerative Medicine, Winston-Salem, NC (US)

( * ) Notice: Subject to any disclaimer, the term of this patent is extended or adjusted under 35 U.S.C. 154(b) by 135 days.

(21) Appl. No.: 14/102,953

(22) Filed: Dec. 11, 2013

(65) Prior Publication Data
US 2014/0099290 A1    Apr. 10, 2014

Related U.S. Application Data

(63) Continuation of application No. 12/712,832, filed on Feb. 25, 2010, now Pat. No. 8,628,572.

(60) Provisional application No. 61/155,760, filed on Feb. 26, 2009.

(51) Int. Cl.
*A61K 35/28*   (2015.01)
*A61K 35/30*   (2015.01)
*A61L 27/54*   (2006.01)
*A61K 35/44*   (2015.01)
*A61F 2/14*    (2006.01)
*A61K 9/00*    (2006.01)
*A61L 27/36*   (2006.01)
*A61L 27/38*   (2006.01)
*A61K 35/12*   (2015.01)

(52) U.S. Cl.
CPC .............. *A61K 35/44* (2013.01); *A61F 2/142* (2013.01); *A61K 9/0051* (2013.01); *A61L 27/3604* (2013.01); *A61L 27/3808* (2013.01); *A61K 35/12* (2013.01); *A61L 2430/16* (2013.01)

(58) Field of Classification Search
CPC . A61F 2/14; A61F 2/142; C12N 5/062; A61L 2430/16; A61L 27/38; A61L 27/3813; Y10S 514/912
See application file for complete search history.

(56) References Cited

U.S. PATENT DOCUMENTS

| 5,827,641 | A | * | 10/1998 | Parenteau | A61F 2/14 424/93.7 |
|---|---|---|---|---|---|
| 6,645,715 | B1 | | 11/2003 | Griffith et al. | |
| 6,753,181 | B2 | | 6/2004 | Atala | |
| 6,866,686 | B2 | | 3/2005 | Ollerenshaw et al. | |
| 6,893,653 | B2 | | 5/2005 | Abraham et al. | |
| 6,893,666 | B2 | | 5/2005 | Spievack | |
| 6,933,103 | B1 | | 8/2005 | Klein et al. | |
| 6,962,814 | B2 | | 11/2005 | Mitchell et al. | |
| 7,883,520 | B2 | * | 2/2011 | Gaeckle | A61F 9/0133 606/166 |
| 8,313,893 | B2 | * | 11/2012 | Wee et al. | 435/1.1 |
| 8,486,139 | B2 | * | 7/2013 | Kishida | A61K 35/12 623/5.11 |
| 2002/0103542 | A1 | * | 8/2002 | Bilbo | A61L 15/40 623/23.72 |
| 2005/0079502 | A1 | | 4/2005 | Hamuro et al. | |
| 2005/0080484 | A1 | * | 4/2005 | Marmo | A61F 9/0017 623/5.14 |
| 2005/0196427 | A1 | * | 9/2005 | Tirrell | A61L 27/227 424/427 |
| 2005/0214259 | A1 | | 9/2005 | Sano et al. | |
| 2005/0256588 | A1 | * | 11/2005 | Sawa | A61L 27/3804 623/23.72 |
| 2006/0099675 | A1 | | 5/2006 | Benard | |
| 2006/0241751 | A1 | * | 10/2006 | Marmo | A61F 9/0017 623/5.11 |
| 2007/0031478 | A1 | | 2/2007 | Kadler et al. | |
| 2007/0137657 | A1 | | 6/2007 | Soll | |
| 2007/0148137 | A1 | * | 6/2007 | Okano et al. | 424/93.7 |
| 2007/0208422 | A1 | | 9/2007 | Walter et al. | |
| 2007/0238173 | A1 | | 10/2007 | Yamagami et al. | |
| 2007/0274968 | A1 | | 11/2007 | Hattori et al. | |
| 2007/0275365 | A1 | | 11/2007 | Lui | |
| 2008/0069399 | A1 | | 3/2008 | Nagao et al. | |
| 2008/0124276 | A1 | * | 5/2008 | Hammond et al. | 424/9.1 |
| 2008/0189050 | A1 | | 8/2008 | Abib | |
| 2009/0142836 | A1 | * | 6/2009 | Wang | A61L 27/3633 435/395 |
| 2009/0202977 | A1 | * | 8/2009 | Ott | C12N 5/0657 435/1.2 |
| 2010/0233240 | A1 | | 9/2010 | Koizumi et al. | |
| 2011/0183404 | A1 | * | 7/2011 | Wee et al. | 435/268 |
| 2011/0244570 | A1 | * | 10/2011 | Birk | C12N 5/0068 435/375 |
| 2011/0293666 | A1 | * | 12/2011 | Wang | A61L 27/3633 424/400 |

FOREIGN PATENT DOCUMENTS

EP    1 980 274 A1    10/2008
WO    WO 2005/038015 A1    4/2005

OTHER PUBLICATIONS

U.S. Appl. No. 14/344,011, filed Dec. 2012, Niu et al.*

(Continued)

*Primary Examiner* — Chang-Yu Wang
(74) *Attorney, Agent, or Firm* — Myers Bigel, P.A.

(57) ABSTRACT

Provided herein is an endothelial scaffold comprising, consisting of, or consisting essentially of decellularized corneal stroma. In some embodiments, the scaffold has cultured endothelial cells seeded thereon. Methods of treating a patient in need of corneal endothelial transplant are also provided, including implanting the scaffold as described herein onto a cornea of the patient (e.g., by deep keratectomy).

10 Claims, 4 Drawing Sheets

(56) References Cited

OTHER PUBLICATIONS

Webb et al., Methods in Cell Science, 2003; 25:167-176.*
Marquez et al. Acta Biomaterialia. 2009;5:1839-1847, published online Feb. 11, 2009.*
Zhang et al. Cell Tissue Res. 2007; 329:249-257.*
Marquez et al. Acta Biomaterialia, 2009; 5:1839-1837, published online on Feb. 11, 2009.*
Webb et al. Method. in Cell Sci. 2003; 25:167-176.*
Amano et al. Mo. Vis. 2008; 14:878-882.*
Gilbert et al. Biomaterials 2006; 27:3675-3683.*
Badylak, Transplant Immunol. 2004; 12:367-377.*
Friend et al. Invest. Ophthalmol. Vis. Sci. 1982; 23:41-49.*
Xu et al. Mol. Vis. 2008; 14:2180-2189.*
Smith JW and Frame J. Observations on the collagen and proteinpolysaccharide complex of rabbit corneal stroma. J. Cell Scl. 1969; 4: 421-436.
Gospodarowicz D et al. Transplantation of cultured bovine corneal endothelial cells to rabbit cornea: Clinical implications for human studies, Proc, Natl. Acad, Sci. USA, Jan. 1979; 76(1): 464-468.
Insler MS and Lopez JG. Heterologous transplantation versus enhancement of human corneal endothelium, Cornea, Mar. 1991; 10(2): 136-48 (Abstract).
Insler MS and Lopez JG. Extended incubation times improved corneal endothelial cell transplantation success. Investigative Ophthalmology & Visual Solent. May 1991; 32(6): 1828-1836.
Meek KM and Fullwood NJ. Corneal and scleral collagens—a microscopist's perspective, Micron, 2001; 32: 261-272.
Toti P et al. CD-34 stromal expression pattern in normal and altered human corneas. Ophthalmology. Jun. 2002; 109(6): 1167-1171.
Price MO and Price, Jr. FW, Descemet stripping with endothelial keratoplasty for treatment of iridocorneal endothelial syndrome. Cornea, May 2007; 26(4): 493-497.
Ruberti JW and Zieske JD, Prelude to corneal tissue engineering—gaining control of collagen organization. Progress in Retinal and Eye Research. 2008; 27: 549-577.
Corneal endothelium, Wikipedia. Dec. 19, 2008: 3 pp.
International Search Report and Written Opinion, PCT/US2010/025398, mailed May 19, 2010.
Ganatra MA, Amniotic membrane in surgery. Journal of Pakistan Medical Association. Jan. 2003; 5 pages.
Ishino Y et al. Amniotic membrane as a carrier for cultivated human corneal endothelial cell transplantation. Investigative Ophthalmology & Visual Science. Mar. 2004; 45(3): 800-806.
Badylak SF. The extracellular matrix as a scaffold for tissue reconstruction. Semin Cell Dev Biol. 2002; 13(5):377-383.

\* cited by examiner

METHODS OF MAKING ENDOTHELIAL SCAFFOLDS

RELATED APPLICATIONS

This application is a continuation of and claims priority to U.S. patent application Ser. No. 12/712,832, filed Feb. 25, 2010, now allowed, which claims the benefit under 35 U.S.C. §119(e) of U.S. Provisional Patent Application Ser. No. 61/155,760, filed Feb. 26, 2009, the disclosure of each of which is incorporated herein by reference in its entirety.

FIELD OF THE INVENTION

The present invention involves scaffolds derived from endothelial tissue and processes for making and using the same.

BACKGROUND

The inner layer of the cornea is a single layer of neural crest-derived endothelial cells (CECs), which form a barrier between the cornea and the aqueous humor and transport water from the corneal stroma. CEC loss can result from eye injuries, complications from cataract surgery (pseudophakic bullous keratopathy (PBK) or aphakic bullous keratopathy (ABK)), and in an inherited condition known as Fuchs dystrophy.

These cells do not divide during adult life. Rather, existing CECs simply spread to compensate for loss or damage. When this spreading is inadequate, vision-impairing corneal opacity results.

Traditional treatment for CEC loss or damage is penetrating keratoplasty (PK), in which a full thickness cadaveric cornea is transplanted onto a recipient eye. However, a procedure known as DSEK (Descemet's Stripping and Endothelial Keratectomy) may be an option in some cases in which the corneal stroma is not scarred. In this procedure, CECs and their underlying basement membrane (Descemet's membrane) are physically removed from the recipient, and only the inner portion of a donor cadaveric cornea, including intact CECs, is transferred to the recipient eye.

More recently, the DMEK procedure (Descemet's Membrane Endothelial Keratoplasty) has been developed, in which the donor cadaveric tissue consists only of Descemet's membrane and CEC layers. Cultured CECs on synthetic films is also under study. These techniques are intended to improve the surgery by eliminating the presence of the posterior stromal tissue from the tissue graft containing CECs. Problems encountered from the stromal thickness include unpredictable refractive error, which may require the patient to wear thick glasses for correction. Presence of the stroma can also create interface haze or scarring. In addition, DMEK may minimize crowding of the anterior chamber to allow future procedures if needed (e.g., anterior chamber intraocular lens and tube shunt).

However, more options are needed to provide suitable alternative tissue sources for the restoration of the corneal endothelial cell layer, as well as the creation or restoration of the endothelial layer of other tissues.

SUMMARY OF THE INVENTION

Provided herein is an endothelial scaffold comprising, consisting of, or consisting essentially of decellularized corneal stroma (e.g., human corneal stroma). In some embodiments, the scaffold has a thickness of between 50 and 200 micrometers.

In some embodiments, the scaffold has cultured endothelial cells seeded thereon (e.g., cultured human corneal endothelial cells). In some embodiments, the cells have been passaged between 1 and 20 times. In some embodiments, the cells are present at a cell density of from 2000 cells/mm$^2$ to 4000 cells/mm$^2$.

A method of treating a patient in need of corneal endothelial transplant is also provided, including implanting the scaffold as described herein onto a cornea of the patient. In some embodiments, the implanting includes performing deep keratectomy.

Also provided is a method of making an endothelial scaffold, including providing sectioned corneal stroma (e.g., human corneal stroma) having a thickness of between 50 and 200 micrometers; and decellularizing said stroma to produce the endothelial scaffold. In some embodiments, cultured endothelial cells (e.g., human corneal endothelial cells) are seeded onto the endothelial scaffold.

Further provided is the use of a scaffold as described herein for the treatment of endothelial disease or injury (e.g., with corneal endothelial transplant). Also provided is the use of a scaffold as described herein for the preparation of a medicament for the treatment of an endothelial disease or injury.

DETAILED DESCRIPTION OF THE PREFERRED EMBODIMENTS

Figure 1:
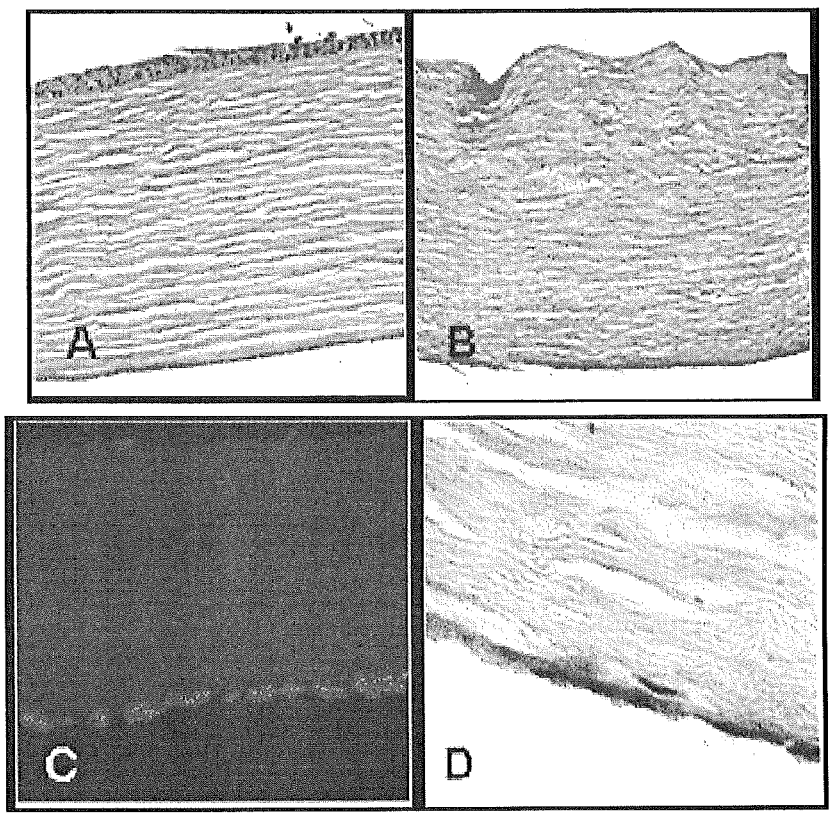
FIG. 1. (A) Native cornea showing the epithelial layer (top blue cells) and the endothelial layer (bottom blue cells (H&E). (B) Decellularized corneal stroma (same orientation) showing a lack of blue (nuclear) staining. (C) Corneal stroma 2 weeks after seeding the decellularized cornea with CECs (DAPI stain) showing a layer of cells adhering and growing on the endothelial surface. (D) Light microscopic view of the re-seeded endothelial layer of the stroma, which contains ZO-1 positive (brown) cells.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Scaffold" as used herein refers to a substrate on which cells can grow. In some embodiments, scaffolds comprise, consist of or consist essentially of corneal tissue, optionally processed (e.g., sectioned, decellularized, shaped (e.g., into a concave form), etc.). These scaffolds are useful in both the medical and research settings. Tissues that may be used to carry out the present invention may be from any suitable animal source, including human, other mammalian (e.g., cat, dog, pig, cow, sheep, horse, monkey), avian (e.g., chicken, turkey, duck, goose, etc.), reptile, amphibian, etc. Tissues may be of any suitable type, including corneal tissue.

"Implanting" as used herein refers to the placement of a biocompatable substrate, such as a scaffold, into a subject in need thereof, with or without prior seeding and/or infiltration of cells. In some embodiments, implanting of a corneal tissue is carried out by full-thickness corneal transplantation (e.g., penetrating keratoplasty (PK)). In other embodiments, implanting is carried out using corneal endothelial keratoplasty procedures (e.g., Descemets stripping endothelial keratoplasty (DSEK), Descemets stripping automated endothelial keratoplasty (DSAEK), deep lamellar endothelial keratoplasty (DLEK), Descemet's membrane endothelial keratoplasty (DMEK), or variations thereof apparent to those of skill in the art, making use of the scaffolds described herein).

As known in the art, the "cornea" is the outermost layer of the eye and is made up of substantially parallel and relatively compacted layers of tissue. Five histiligically distinct layers are found: the epithelial layer, the Bowman's layer, the stroma, the Descemet's membrane, and the endothelial layer.

The outermost layer of the cornea is the epithelial layer, a protective layer of tissue that regenerates if injured. Moving inwardly towards the center of the eye is the acellular base surface of the epithelial layer, known as "Bowman's membrane." Immediately inward from the Bowman's membrane is the "stroma" of the cornea, which is an extracellular collagen architectural matrix with scattered keratocytic cells. The stroma layer is bounded at its deepest level by a cuticular, cellular membrane known as "Descemet's membrane." Finally, the inner layer of the cornea is a monolayer of neural-crest derived cells called the cornea "endothelium," made up of corneal endothelial cells (CECs), which form a barrier between the cornea and the aqueous humor of the eye. The CECs aid in maintaining the transparency of the cornea by regulating corneal water content.

"Corneal tissue" as used herein is tissue isolated or harvested from the cornea. In some embodiments, corneal tissue comprises, consists of or consists essentially of tissue isolated or harvested from the stroma layer of the cornea. "Isolated" as used herein signifies that the cells are placed into conditions other than their natural environment. Tissue or cells are "harvested" when initially isolated from a subject, e.g., a primary explant. Corneal tissue "consisting essentially of" tissue isolated or harvested from the stroma layer of the cornea is 90, 95, 98, 99 or 99.5 percent or more by weight stroma and 10, 5, 2, 1 or 0.5 percent or less by weight and/or volume of non-stroma tissue, e.g., Descement's membrane, Bowman's membrane and/or epithelial cells.

The corneal "stroma" is the thickest layer of the cornea (approximatly 90% of the cornea thickness), composed of parallel collagen fibers (mostly type I and type VI) and sparse keratocytes, and lies between the Bowman's membrane and the Descemet's membrane. In some embodiments, corneal stroma is "decellularized" to remove existing cells prior to or after sectioning to produce a scaffold as described herein.

"Corneal endothelial cells" or "CECs" are cells possessing the characteristics of endothelial cells normally found in the corneal endothelial cell layer. They are distinguished from other endothelial cells by the expression of both endothelial and epithelial markers, namely, one or more of the following: Zona occludin-1 (ZO-1), Na+/K+ ATPase, connexin-43, AE1/AE3, von Willebrand factor (vWF), and VE-Cadherin, but do not express CD31. In addition, CECs possess the functional abilities to 1) form a single-cell thick layer ("monolayer") on the inner surface of the cornea in a hexagonal pattern, 2) form a barrier between the cornea and the aqueous humor of the eye and regulate water flow therebetween, and 3) pump excess liquid from the cornea into the aqueous humor. In some embodiments, cells are isolated or harvested from the corneal endothelial layer. In some embodiments, CEC are derived from corneal progenitor cells (e.g., isolated or harvested from the corneal limbus). In some embodiments, CECs are isolated or harvested from the posterior surface of the peripheral cornea and limbus (e.g., strip the endothelium and Descemet's membrane from the posterior cornea and place into collagenase to free the cells from the Descemet's membrane).

"Differentiated" refers to cells or a population containing cells that have specialized functions. In this sense they are not progenitor or stem cells. For example, cells differentiated to become CECs as described herein are capable of forming a monolayer of hexagonally-shaped cells that form a barrier and pump water from the cornea, and express known markers of differentiated CECs, e.g., corneal endothelial cell markers Zona occludin-1 (ZO-1) (marker for tight junctions), Na+/K+ ATPase (an enzyme used to pump water out of CECs and clarify the cornea), connexin-43 (gap junction marker) cytokeratin AE1/AE3, von Willebrand factor (vWF), and/or VE-Cadherin (vascular endothelial cadherin, or Cadherin 5 (CD5), marker of cell-cell junctions).

In some embodiments, cells are syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject or patient to be treated) and isogeneic (i.e., a genetically identical but different subject, e.g., from an identical twin). Cells may be obtained from, e.g., a donor (either living or cadaveric) or derived from an established cell strain or cell line. Cells may be harvested from a donor, e.g., using standard biopsy techniques known in the art.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects may also include animal subjects, particularly mammalian subjects such as canines, felines, bovines, caprines, equines, ovines, porcines, rodents (e.g., rats and mice), lagomorphs, non-human primates, etc., for, e.g., veterinary medicine, laboratory and/or pharmaceutical drug development purposes.

"Cultured" cells are isolated from tissue and expanded in controlled conditions known the art (e.g., 37° C., 5% $CO_2$), usually in a culture vessel. The "primary culture" is the first culture to become established after seeding disaggregated cells or primary explants into a culture vessel. "Expanding" as used herein refers to an increase in number of viable cells. Expanding may be accomplished by, e.g., "growing" the cells through one or more cell cycles, wherein at least a portion of the cells divide to produce additional cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous for one or more desirable characteristics.

In some embodiments, harvested cells are not passaged. In other embodiments, cells are passaged once, twice, or three times. In still other embodiments, cells are passaged more than 3 times. In some embodiments, cells are passaged 0 to 1, 0 to 2 or 0 to 3 times. In some embodiments, cells are passaged 1 to 2, 1 to 3, or 1 to 4 or more times. In some embodiments, cells are passaged 2 to 3 or 2 to 4 or more times. In further embodiments, cells are passaged 5, 8, 10, 12 or 15 or more times. In some embodiments, cells are passaged 0, 1, 2, 3 or 4 to 8, 10, 15 or 20 or more times.

Alternatively, in other embodiments, cells are cultured to produce cell lines, which may later be differentiated to produce more specialized cells. The establishment of "cell lines," as opposed to cell strains, are by and large undifferentiated, though they may be committed to a particular lineage. Propagation naturally favors the proliferative phenotype, and in some embodiments cells may require a reinduction of differentiation by, e.g., alteration of the culture conditions. There are a number of differentiation factors known in the art that may induce differentiation in cell lines (e.g., cytokines such as epimorphin and HGF, vitamins, etc.).

Scaffolds and Methods of Making the Same

In some embodiments, scaffolds useful for endothelial implantation comprises, consists of or consists essentially of corneal tissue. The corneal tissue in some embodiments is human tissue harvested from a cadaveric donor. In some embodiments, the corneal tissue is sectioned stroma (e.g., between 50 and 200 μm, or between 75 and 150 μm, or between 100 and 130 μm average thickness), such that multiple scaffolds may be created from one donor cornea (e.g., 3 or 4 per donor cornea). A microtome may be used for the sectioning (e.g. with a 110 μm blade).

In some embodiments, harvested or isolated tissue is processed to remove cells ("decellularized"). Methods for removing cells from tissues are known in the art (see, e.g., Badylak (2002) *Semin Cell Dev Biol* 13(5):377-83; U.S. Pat. No. 6,893,666; U.S. Pat. No. 6,962,814; U.S. Pat. No. 6,893,653; U.S. Pat. No. 6,866,686; U.S. Pat. No. 6,753,181; U.S. Pat. No. 6,933,103). A typical method uses a hypo-osmotic solution such as deionized water to burst the cells, followed by a detergent solution, perhaps in combination with an enzyme for disrupting cell adhesion, to remove the cellular debris. A third step is often extraction with a mild basic solution to remove anionic materials such as DNA. The detergent and basic solution may be combined into a single step for convenience, Optimization of the decellularization may be performed to determine the conditions that best preserve the optimal mechanical and biochemical properties of the scaffold. In some embodiments, stromal layers may be decellularized by immersing in a 2% Triton X-100 (v/v) (Sigma, T9284) and 0.1% $NH_4OH$ (v/v) (Fisher Scientific, Inc., A669-212) solution with gentle shaking at 4° C. for 72 hours.

In some embodiments, scaffolds produced by the process of decellularizing stromal tissue (optionally sectioned prior to or after decellularizing) have the following characteristics. Upon gross exam, the scaffold would look similar to a scaffold derived from amniotic membrane. However, upon touching the scaffold with a Weck Cell sponge, one side of the amnion would be sticky, while the other side would be slick. The decellurized corneal stroma tissue would be normal and non-sticky, as well as more stiff and/or less flaccid. With microscopic exam, one skilled in the art can easily tell them apart.

Scaffolds produced by the process of decellularizing stromal tissue (optionally sectioned prior to or after decellularizing) according to some embodiments also have the following characteristics. Regarding collagen composition, Type I collagen is the major component, comprising between 50 and 90, or between 60 and 80, or approximately 68% of the dry weight of the decellularized scaffold (prior to optional cell seeding), in accordance with its natural occurance in the cornea. In addition, collagen Types III, V, VI, VIII, XII and XIV have all been detected in the corneal stroma, and also may be detected in the scaffolds.

The collagen fibrils are surrounded by a matrix containing proteoglycans (sulphated glycosaminoglycans attached to a protein core) and various other proteins. The collagen fibrils are laid down in lamellae that lie roughly parallel to the planar surface. Transparency is a consequence of the detailed ultrastructure of the tissue and has been attributed to the narrow, uniform diameter collagen fibrils, and to the regularity of their lateral packing. In these two respects, the corneal stroma is a unique connective tissue. Therefore, in some embodiments, structural parameters and mechanical properties are consistent with that known for the corneal stroma as found in the eye, including the collagen fibril direction (which governs the tensile strength at any point in the tissue) and the fibril diameters and organization (see, e.g., Meek, K M. Corneal and scleral collagen—a microscopist's perspective. Micron Volume 32, Issue 3, April 2001).

In some embodiments, scaffolds further include Type IV collagen. The major structural component of the basement membrane (BM) (e.g., Descemet's membrane) is type IV collagen. To date, six different α(IV) chains have been identified (Sado et al 1995). A polyclonal anti-human collagen IV antibody is expressed in all ocular surface epithelial and endothelial basement membranes without any distinct regional differences. However, when using chain-specific antibodies, clear regional differences can be observed. The α1(IV) and the α2(IV) chains are weakly expressed or absent in the corneal BM, but strongly expressed in the limbus and conjunctiva. In contrast, an abrupt decrease in immunoreactivity of the limbal BM as compared to the corneal BM can be found for the α3(IV) chain, whereas the immunoreactivity for the α4(IV) chain is generally weak or lacking in all basement membranes. Both α5(IV) and α6(IV) chains show a uniformly strong labeling of corneal and limbal BMs and gradually decreased staining intensity posteriorly in the conjunctival BM.

The scaffolds may also include laminin, fibronectin, nidogen, decorin, versican, etc., or combinations thereof. Laminins are the major non-collagenous corneal stroma constituents. Of the different subunits, laminin-1 and laminin-5 are uniformly distributed in the corneal stroma. The insoluble form of fibronectin serves as a general cell adhesion molecule, and its expression is particulary strong at the endothelial face of the cornea. Both nidogen isoforms, nidogen 1 and 2, also known as entactin 1 and 2, are ubiquitous BM glycoproteins, which play a crucial role in BM assembly by connecting the collagen IV and laminin networks (Schlotzer-Schrehardt et al 2007). Both isoforms, particularly nidogen-2, are most intensely expressed in the limbal and conjunctival BMs as compared to the corneal epithelial BM. Decorin is a member of the small leucine-rich proteoglycan superfamily. In diseased corneas, it is seen on the endothelial face of the basement membrane. Versican is a large chondroitin sulfate proteoglycan of the extracellular matrix, which regulates cell phenotype and behaviour including cell adhesion, cell proliferation, and cell migration. Thus, versican may be useful for evaluating the potential health of seeded cells.

Without wishing to be bound by theory, our results indicate that isolated CECs, when grown on extracellular matrix molecules (ECM) that most closely mimic that naturally found in the cornea's stroma, the CECs markedly expand, express markers of functionality and form monolayers. Native corneal ECM promotes cell growth and mantenance of CEC properties which have the potential of producing fully functional, long-lasting corneal transplants.

In some embodiments, a comparison between native corneal stromas and decellularized stromas show similar mechanical behavior. For example, the ultimate tensile strength of decellularized stroma at 37 degrees Celsius and/or at room temperature may be between 2 and 20 MPa, or between 5 and 15 MPa, or between 8 and 12 MPa, similar to that of native corneal stroma. In some embodiments, elongation at break of decellularized stroma at 37 degrees Celsius and/or at room temperature is similar to that of native stroma, e.g., between 10 and 50%, or between 20 and 40%, or between 25 and 35%. In some embodiments, Young's modulus of decellularized stroma at 37 degrees Celsius and/or at room temperature is similar to that of native stroma, e.g., between 30 and 70 MPa, or between 40 and 60 MPa, or between 45 and 55 MPa.

In some embodiments, the scaffold may be provided in a pharmaceutically acceptable carrier (e.g., phosphate buffered saline (PBS)). "Pharmaceutically acceptable" means that the carrier is suitable for administration to a subject to achieve the treatments described herein, without unduly deleterious side effects. In some embodiments, the prepared scaffold may be frozen in a medium before use. For example, the scaffold may be frozen in a liquid mixing equal volume ratio of DMEM (Dulbecco's modified Eagle's medium) and glycerol at −80° C.

Cell Harvest, Culture and Seeding

In some embodiments, human CECs are harvested from the cornea of the patient or from an appropriate donor using methods known in the art. For example, the Descemet's membrane and the endothelial cell layer of the corneal tissue are peeled off from the corneal stroma, then transferred to a culture dish and treated with collagenase or dispase to separate the CECs from the Descemet's membrane (this may be aided mechanically by gentle pipetting). The Descemet's membrane is removed, and the CECs are cultured in an appropriate culture solution. The culture solution can be, for example, DMEM (Dullbecco's Modified Eagle's Medium) to which FBS (fetal bovine serum), b-FGF (basic-fibroblast growth factor), EGF (epidermal growth factor), insulin and antibiotics such as penicillin and streptomycin are added. A culture container (culture dish) may be used in which the surface is coated with type I collagen, type IV collagen, fibronectin, laminin and/or extracellular matrix of bovine endothelial cells, to promote cell attachment.

In some embodiments, harvested corneas are placed in a dish containing 0.02 g collagenase II in 10 mL PBS and incubated at 37° C. for 90 minutes. Sterile forceps and a spatula are then used to gently scrape the scleral rim of Descemet's membrane with intact endothelium. Cells removed by this process are centrifuged for 5 minutes at 1500 rpm and then resuspended in 2.5 mL EGM-2 complete culture medium containing 10% FBS and plated in the wells of a 6-well tissue culture dish. In some embodiments, EGM-2 may be supplemented with growth factors, antibiotics, etc., as desired. For example, EMG-2 supplemented with epidermal growth factor (EGF), insulin-like growth factor (IGF), vasular endothelial growth factor (VEGF), fibroblast growth factor (FGF), hydrocortisone, gentamicin, amphotericin-B, etc., or combinations thereof, may be used. According to some embodiments, CECs cultured in petri plates with no coating, fibronectin coating, or collagen type IV coating can be used. Subculturing may be performed by enzymatic treatment (e.g., 0.05% trypsin-EDTA (Gibco)) of the cells followed by reseeding (e.g., at a density of approximately 3500 cells/cm$^2$).

In some embodiments, Descemet's membrane and endothelium are stripped from the cornea using fine forceps, a spatula and/or a bent needle under a surgical microscope, and the endothelium, alone, is digested prior to seeding the culture plate, to minimize the growth of unwanted cells (mainly fibroblasts) in the culture.

In some embodiments, after the corneal endothelial cells used for culture are expanded, a subculture of the cells is carried out when cells become subconfluent or confluent. The subculture may be carried out as known in the art. For example, cells are detached from the surface of the culture container by treating with trypsin-EDTA and then collected. Culture solution is added to the collected cells to create a cell suspension. Centrifugation can be carried out when or after cells have been collected to provide a high cell density of cells. Common conditions for centrifugation include 500 rpm (30 g) to 1000 rpm (70 g) and 1 to 10 minutes.

As in the above-mentioned initial culture, a cell suspension can be plated on the culture container and cultured. The subculture can be carried out in the same culture conditions as the above-mentioned initial culture. The culture time may differ depending upon the cells used, but is generally 7 to 21 days. By repeating the subcultures, the number of cells can be increased and a cell suspension with a high cell density can be prepared.

The cell suspension may be seeded onto a scaffold and optionally further cultured on the scaffold. The number of cells may be adjusted so that a cell layer with a desired cell density can be formed for implantation. In some embodiments, 3000 cells/mm$^2$ to 7500 cells/mm$^2$ or 5000 cells/mm$^2$ to 7500 cells/mm$^2$ are plated so that a cell layer with a cell density of about 2000 cells/mm$^2$ to 4000 cells/mm$^2$ is formed. The culture may be carried out under the same conditions as in the above-mentioned initial culture.

Seeding of the corneal endothelial cells on the scaffold can be carried out, for example, by the following procedures. First, a container with a bottom face made of membrane with a suitable pore size through which culture solution can pass (hereafter referred to as a "culture insert") is placed with the bottom face faced downward. A scaffold as described herein may then be placed on the bottom face of the culture insert (drying treatment may be carried out once in this state), then setting this culture insert in a culture container, and finally plating and culturing the cell suspension. An example of a membrane that can be used for the bottom face of the culture insert includes a commercially available polycarbonate or polyester membrane, having a pore size of about 0.4 μm to 3.0 μm. Centrifugation (e.g., 500 rpm (30 g) to 1,000 rpm (70 g) and 1 to 10 minutes) may be carried out after the cell suspension is plated in the culture insert to increase the cell density on the scaffold and promote adhesion.

In further embodiments, cultured CECs can be plated onto dishes in a DMEN-F12 medium containing 10% FCS, 5% CS, 5% Dextran, 300 μg/ml glutamine, 2.5 μg/ml Amphotericin B, and 50 ng/ml bFGF. At confluency, (7 to 10 days post seeding), the dishes are treated with 20 mM NH$_4$OH at a volume sufficient to cover at least ⅔ of the plate. After 5 minutes of shaking in a mechanical shaker, the NH$_4$OH is aspirated and the dish rinsed 5 times with PBS. Laminin and fibronectin is dissolved in distilled water at a concentration of 100 μg/ml. Type IV collagen is dissolved in 0.6% v/v acetic acid/water. Laminin, fibronectin, and type IV collagen are added to the ECM plates as needed for culture purposes.

In some embodiments, a cloning ring or cloning cylinder is used to hold the cell suspension on the scaffold, keeping the cell suspension from flowing away from the scaffold during seeding.

In some embodiments, prior to seeding the cells onto the implant, one or more attachment proteins selected from fibronectin (e.g., ranging from 0.1 μg to 500 μg/ml in PBS), laminin (e.g., 0.1 μg to 500 μg/ml in PBS), RGDS (e.g., 0.01 μg to 100 μg/ml in PBS), collagen type IV (e.g., ranging from 0.1 μg to 1000 μg in 0.1 M acetic acid) is added to the scaffold surface and incubated at 4° C. for a period ranging from 5 to 60 minutes. The residual proteins are removed after the incubation period, and the scaffold is rinsed (e.g., three times with PBS) and optionally placed on a concave holder.

In some embodiments, cultured human endothelial cells can be removed from the tissue culture dish with 0.05% trypsin and 0.02% EDTA in saline solution. The cell suspension may be counted according to methods known in the art, e.g. with a Coulter Particle Counter (Z1 model, Beckman-Coulter), and a preparation of about 50,000 to 500,000 cells/ml, or about 200,000 cells in 200 μl of culture medium (DME-H16 with 5% fetal calf serum or a serum-free medium containing a mixture of attachment proteins such as fibronectin, laminin, and fibroblast growth factors (at 10 ng to 400 ng/ml) may be added carefully onto the denuded corneal button. A layer of 1% sodium hyaluronate, such as Healon® (Advanced Medical Optics, Santa Ana, Calif.) at approximately 0.1 to 0.5 ml, may be layered onto the cell suspension as a protectant. The scaffold can then be incubated at 37° C. in a 10% CO$_2$ incubator for a period of 10 minutes up to 24 hours. Alternatively, the coated scaffold will be incubated for 20 minutes and the cornea will be rinsed three times with PBS at 25° C. and ready for implantation.

Further methods of CEC cell culture are found in U.S. Patent Application Publication Nos. 2007/0275365 to Lui and 2005/0214259 to Sano et al., which are incorporated herein by reference.

Methods of Treatment

In some embodiments, a scaffold described herein is implanted into the inner layer of the cornea of a subject in need thereof according to surgical methods known in the art (e.g., using the DSEK technique). In other embodiments, a scaffold described herein is implanted into another area of the body, e.g., serving as a vascular tissue implant, etc. In some embodiments, the scaffold includes cells seeded thereon (e.g., CECs as described herein).

"Treat" refers to any type of treatment that imparts a benefit to a patient, e.g., a patient afflicted with a disease that affects endothelial cells (e.g., corneal endothelial cells, such as Fuchs dystrophy), a patient having endothelial injury (e.g., to the endothelial layer of the cornea), etc. Treating includes actions taken and actions refrained from being taken for the purpose of improving the condition of the patient (e.g., the relief of one or more symptoms), delay in the onset or progression of a disease, etc.

Corneal implantation methods can include full thickness trepanation (PK) and deep keratectomy. In the PK method, full thickness corneal button is obtained using a trephine, and the corneal endothelial cell layer is replaced by a scaffold (seeded with CECs), resulting in a full thickness cornea to attach for the recipient. Specifically, the method can be carried out as follows. First, incision of the full thickness cornea of a recipient (host) is carried out by using a trephine, and a part (or the whole) of the cornea is collected as a button shape. Then, from the piece of cornea collected, the Descemet's membrane and a corneal endothelial cell layer are peeled off. The corneal implant is then attached to the exposed corneal stroma. Thereafter, the corneal graft is returned to the recipient and fixed with sutures.

For deep keratectomy, instead of extracting the full thickness of the cornea, only the deep portion of the cornea is excised. First, a part of the recipient's corneal stroma is delaminated, and the posterior part of corneal stroma and the Descemet's membrane or the endothelial cell layer are excised. Typically, only the endothelial cell layer or only the endothelial cell layer and Descemet's membrane are peeled and excised. Next, the implant seeded with CECs is inserted into the excised portion by using a spatula. If desired, air is pumped into the anterior chamber to aid in attaching the implant to the recipient cornea.

Certain embodiments are further described in the following non-limiting examples.

EXAMPLES

Example 1

Cornea Decellularization

Corneal scaffolds were made using a microtome to cut whole corneas (obtained from the eye bank) into 125 micron-thick slices cut parallel to the endothelial surface. These corneal slices were placed in decellularization solution (2% Triton X100, 0.1% $NH_4OH$) for 3 days at 4° C. A native cornea (A) and a decellularized cornea (B) are shown in FIG. 1. The decellularization process removed the epithelial, endothelial, and 95% of the stromal cells. These decellularized sections were stored in PBS and kept at a 4° C. until they were used for cell seeding experiments.

Example 2

Corneal Endothelial Cells (CECs)

Human CECs were collected from the basal surface of the limbus of cadaver corneas of donors 14-75 years old. The corneas were placed in a petri dish containing 0.02 g collagenase II in 10 mL PBS for each rim and incubated at 37° C. for 90 minutes. Sterile forceps and a spatula were then used to gently scrape the scleral rim of Descemet's membrane with intact endothelium. Cells removed by this process were centrifuged for 5 minutes at 1500 rpm and then resuspended in 2.5 mL EGM-2 complete culture medium containing 10% FBS and plated in the wells of a 6-well tissue culture dish.

Figure 2:
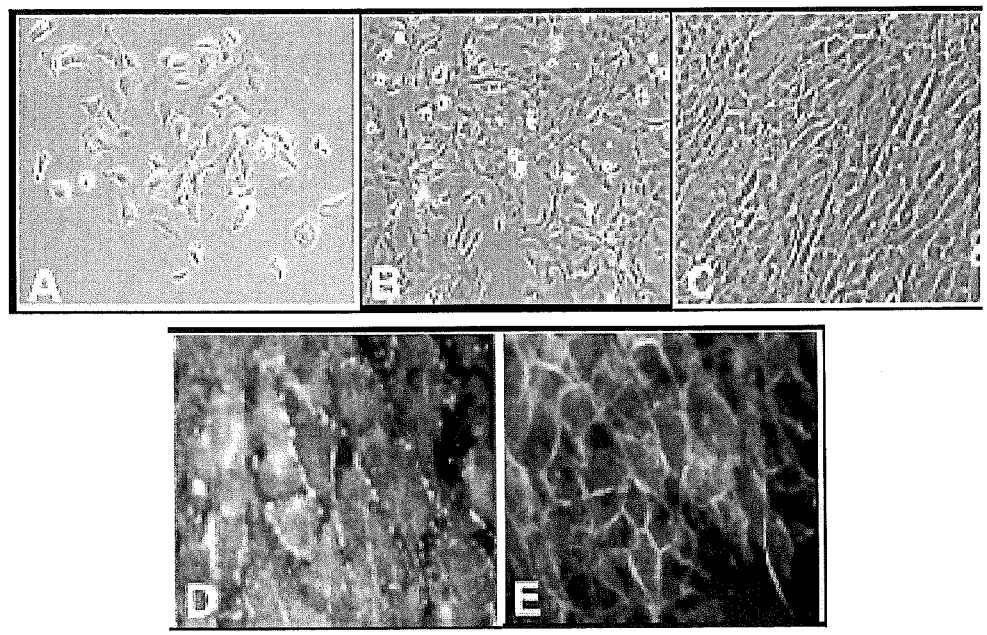
FIG. 2. Corneal endothelial cells were removed from the scleral rim and cultured in EGM+10% FBS for 6 days, 12 days, and 18 days (A, B, and C) (100×). Confluent CECs stained with Zona Occludin-1 (D)—beaded green color around the periphery of the cells, and Na+/K+ ATPase (E)—green color around the periphery of the cells (640×).
Figure 3:
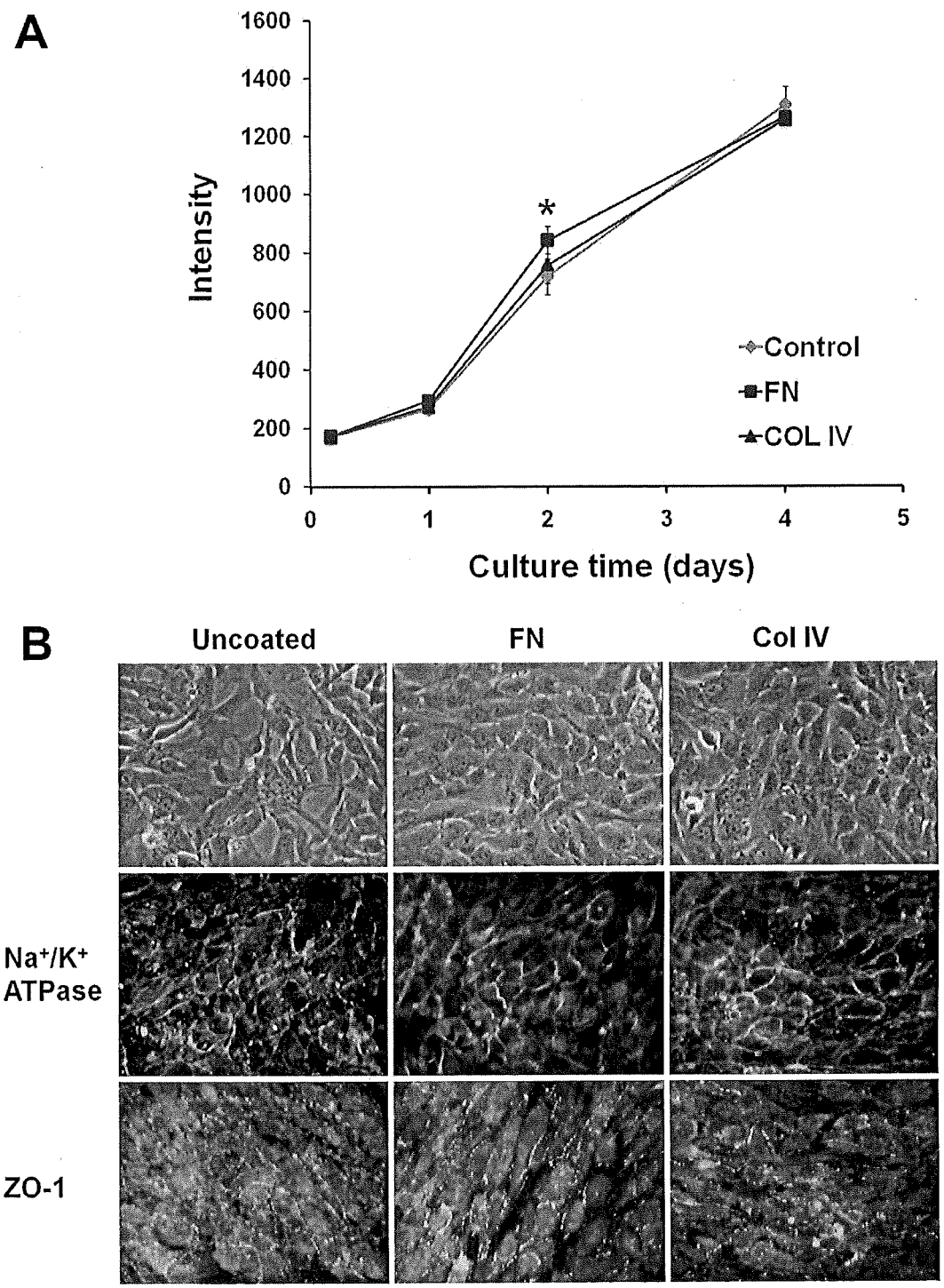
FIG. 3. (A) Growth rate of HCEC grown on uncoated culture plates (control), fibronectin (FN), and type IV collagen (Col IV) at 1, 2, and 4 days post seeding (as assayed by MTS intensity). *P<0.05 between FN and control. (B) Expression on Na$^+$/K$^+$ ATPase and zona occludens-1 (ZO-1) in CECs coated on tissue culture plates or plates coated with fibronectin, or type IV collagen (magnification, ×400).
Figure 4:
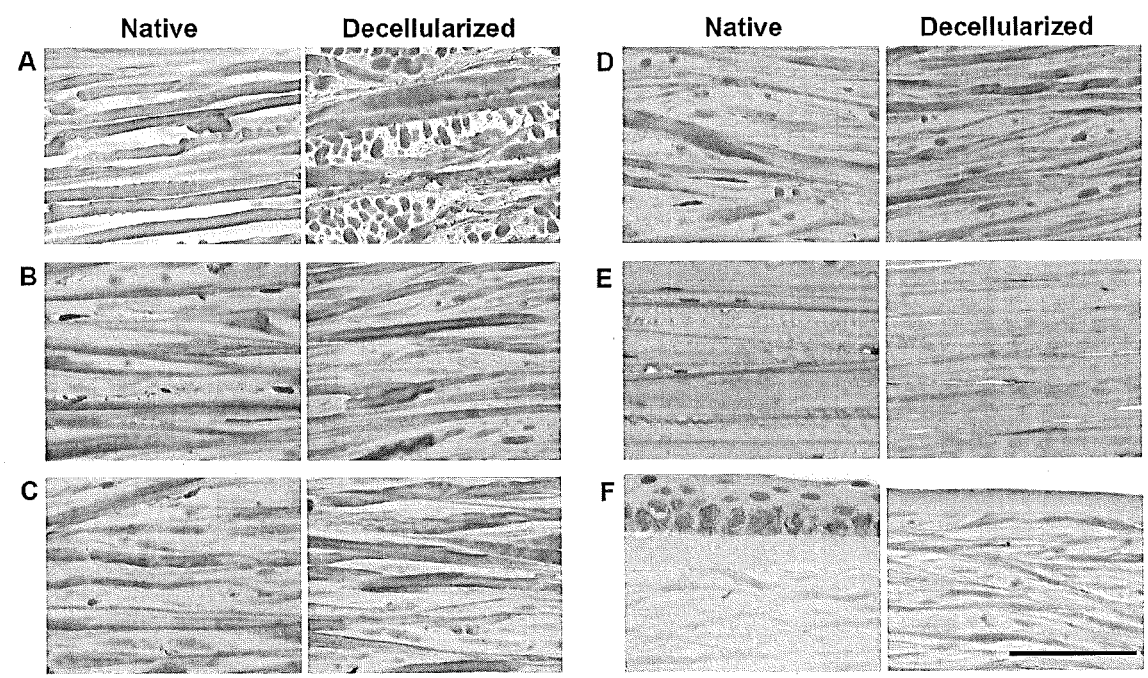
FIG. 4. Immunohistological evaluation of human corneal stromas before and after decellularization; (A) collagen I, (B) collagen II, (C) collagen III, (D) collagen IV, (E) fibronectin, and (F) laminin. Scale bar indicates 50 µm.

Type IV collagen is a major component of the corneal stroma and fibronectin is an adhesive protein that is often used to coat endothelial cell-seeded culture plates. To test if the presence of extracellular matrix components affected growth rates, we plated cells on petri plates with no coating, fibronectin coating, or collagen type IV coating. There were no differences in growth rates and initial colonies of endothelial-phenotype cells were noted at 6 days post-isolation. These cells routinely grew to confluence in 18 days (FIGS. 2A, B and C). At 2 days after seeding, there were significantly more HCEC on the fibronectin-coated plates compared to the others (P<0.05). However, 4 days after seeding, there were no significant differences in cell numbers among each growth condition (FIG. 3A). Seeded cells on each plate were grown to confluence and analyzed for expression of the tight junction marker ZO-1 and $Na^+/K^+$ ATPase, which is a marker of the cellular ability to pump water from the cornea (FIG. 3B). Cells grown on all culture plate types expressed ZO-1 and $Na^+/K^+$ ATPase. However, the cells on the collagen IV- and fibronectin-coated plates showed better cellular morphology, including shape and organization typical of CECs.

The doubling times of these cells varied from 22 hours to 50 hours (n=5 cultures) with the shorter doubling times corresponding with cultures that were able to be passaged a greater number of times (approximately 8 passages) while maintaining consistent doubling times and thus greater expansion capabilities. CECs were more readily obtained from younger donors and the doubling time of cultures obtained from donors over 60 years old was significantly increased. However, despite the slower growth characteristics of these cultures, confluence was obtained in these groups and cell morphology appeared normal. These data indicate that while viable cultures can be obtained from donors over the age of 60, the quality of the cultures may not be optimal for use in tissue engineering applications.

Cultures were remarkably pure, with little stromal cell contamination. To further characterize the cells, immunocytochemistry was used to identify cell markers consistent with those of known corneal endothelial cells. Zona occludin-1 (ZO-1) (FIG. 2, D), and Na+/K+ ATPase (FIG. 2, E), an enzyme involved in pumping water out of CECs to clarify the cornea, were observed. These cells also expressed AE1/AE3, connexin-43, VE-Cadherin, and vWF, and were negative for CD31, as expected (data not shown). All expression data were consistent with the known profile for corneal endothelial cells.

Results indicate that CECs can be collected from cadaver corneas, expanded and characterized. These cells express tight junction markers and functional markers consistent with corneal endothelial cells.

Additional corneal endothelial cells were obtained as listed below in Table 1, along with the cell isolation process used.

Human Corneal Endothelial Cell Isolation

| Isolation date | Sample # | ID # | Donor Death | Post-mortem preservation | Preparation | Age | Remark | |
|---|---|---|---|---|---|---|---|---|
| Aug. 15, 2008 | H001 | OSI-1148-08 | Aug. 8, 2008 | | | 55 | Scleral rim | 0.2% collagenase(II) for 1½ hr |
| Aug. 15, 2008 | H002 | OSI-1151-08 | Aug. 10, 2008 | | | 68 | Scleral rim | 0.2% collagenase(II) for 1½ hr |
| Aug. 15, 2008 | H003 | OSI-1141-08 | Aug. 7, 2008 | | | 56 | Scleral rim | 0.2% collagenase(II) for 1½ hr |
| Aug. 15, 2008 | H004 | OSI-1153-08 | Aug. 8, 2008 | | | 59 | Scleral rim | 0.2% collagenase(II) for 1½ hr |
| Aug. 15, 2008 | H005 | OSI-1143-08 | Aug. 8, 2008 | | | 39 | Scleral rim | 0.2% collagenase(II) for 1½ hr |
| Aug. 20, 2008 | H006 | OSI-1182-08 | Aug. 14, 2008 | 2008 Aug. 14 | 2008 Aug. 18 | 64 | Scleral rim | 0.2% collagenase(II) for 1½ hr |
| Aug. 20, 2008 | H007 | OSI-1193-08 | Aug. 15, 2008 | 2008 Aug. 16 | 2008 Aug. 18 | | Scleral rim | 0.2% collagenase(II) for 1½ hr |
| Aug. 20, 2008 | H008 | OSI-1181-08 | Aug. 14, 2008 | 2008 Aug. 14 | 2008 Aug. 18 | | Scleral rim | 0.2% collagenase(II) for 1½ hr |
| Aug. 20, 2008 | H009 | OSI-1192-08 | Aug. 15, 2008 | 2008 Aug. 16 | 2008 Aug. 18 | 73 | Scleral rim | 0.2% collagenase(II) for 1½ hr |
| Aug. 27, 2008 | H010 | OSI-1243-08 | 2008 Aug. 19 | 2008 Aug. 20 | 2008 Aug. 25 | 63 | Scleral rim | explant on tissue culture dish |
| 2008 Aug. 27 | H011 | OSI-1244-08 | 2008 Aug. 21 | 2008 Aug. 21 | 2008 Aug. 26 | 56 | Scleral rim | explant on tissue culture dish |
| 2008 Aug. 27 | H012 | OSI-1245-08 | 2008 Aug. 21 | 2008 Aug. 21 | 2008 Aug. 26 | 56 | Scleral rim | explant on tissue culture dish |
| 2008 Sep. 09 | H013 | OSI-1260-08 | 2008 Aug. 26 | 2008 Aug. 26 | 2008 Sep. 01 | 50 | Scleral rim | 0.02% EDTA for 1 hr |

-continued

Human Corneal Endothelial Cell Isolation

| Isolation date | Sample # | ID # | Donor Death | Post-mortem preservation | Preparation | Age | Remark | |
|---|---|---|---|---|---|---|---|---|
| 2008 Sep. 09 | H014 | OSI-1261-08 | 2008 Aug. 26 | 2008 Aug. 26 | 2008 Sep. 01 | 50 | Scleral rim | 0.02% EDTA for 1 hr |
| 2008 Sep. 09 | H015 | OSI-1266-08 | 2008 Aug. 26 | 2008 Aug. 27 | 2008 Sep. 01 | 14 | Scleral rim | 0.02% EDTA for 1 hr |
| 2008 Sep. 09 | H016 | OSI-1267-08 | 2008 Aug. 26 | 2008 Aug. 27 | 2008 Sep. 01 | 14 | Scleral rim | 0.2% collagenase(II) for 1½ hr |
| 2008 Sep. 09 | H017 | 08-0172-1w | 2008 Aug. 27 | 2008 Aug. 27 | | 70 | Scleral rim | 0.2% collagenase(II) for 1½ hr |
| 2008 Sep. 09 | H018 | OSI-1297-08 | 2008 Sep. 03 | 2008 Sep. 03 | 2008 Sep. 08 | 72 | Scleral rim | 0.2% collagenase(II) for 1½ hr |
| 2008 Sep. 09 | H019 | OSI-1310-08 | 2008 Sep. 03 | 2008 Sep. 03 | 2008 Sep. 09 | 72 | Scleral rim | 0.2% collagenase(II) for 1½ hr |
| 2008 Sep. 15 | H020 | 09092008-018 OD1 | 2008 Sep. 09 | 2008 Sep. 10 | | 65 | Scleral rim | 0.02% EDTA for 1 hr/trypsin |
| 2008 Sep. 15 | H021 | OSI-1351-08 | 2008 Sep. 10 | 2008 Sep. 10 | 2008 Sep. 15 | 33 | Scleral rim | 0.2% collagenase(II) for 1 hr |
| 2008 Sep. 15 | H022 | OSI-1341-08 | 2008 Sep. 11 | 2008 Sep. 11 | 2008 Sep. 15 | 69 | Scleral rim | 0.2% collagenase(II) for 1 hr |
| 2008 Sep. 15 | H023 | OSI-1350-08 | 2008 Sep. 11 | 2008 Sep. 11 | 2008 Sep. 15 | 74 | Scleral rim | 0.2% collagenase(II) for 1 hr |
| 2008 Sep. 15 | H024 | OSI-1360-08 | 2008 Sep. 12 | 2008 Sep. 12 | 2008 Sep. 16 | 70 | Scleral rim | 0.2% collagenase(II) for 1 hr |
| 2008 Sep. 25 | H025 | OSI-1385-08 | 2008 Sep. 17 | 2008 Sep. 17 | 2008 Sep. 22 | 65 | Scleral rim | 0.2% collagenase(II) for 1½ hr/FN coated |
| 2008 Sep. 25 | H026 | OSI-1402-08 | 2008 Sep. 18 | 2008 Sep. 18 | 2008 Sep. 23 | 76 | Scleral rim | 0.2% collagenase(II) for 1½ hr/FN coated |
| 2008 Sep. 25 | H027 | 2008-09-71 | 2008 Sep. 18 | 2008 Sep. 18 | | 76 | Scleral rim | 0.2% collagenase(II) for 1½ hr/FN coated |
| 2008 Sep. 25 | H028 | OSI-1390-08 | 2008 Sep. 19 | 2008 Sep. 19 | 2008 Sep. 22 | 21 | Scleral rim | 0.2% collagenase(II) for 1½ hr/FN coated |
| 2008 Oct. 01 | H029 | OSI-1422-08 | 2008 Sep. 24 | 2008 Sep. 24 | 2008 Sep. 28 | 72 | Scleral rim | 0.2% collagenase(II) for 1½ hr/FN coated |
| 2008 Oct. 01 | H030 | 2008-09-106 | 2008 Sep. 26 | | | 63 | Scleral rim | 0.2% collagenase(II) for 1½ hr/FN coated |
| 2008 Oct. 01 | H031 | 08-0191-200 | 2008 Sep. 24 | 2008 Sep. 25 | | 8 | Scleral rim | |

Thirty-seven samples in total were examined and classified into three groups based on the age of the corneal donor: (1) below 30 years old, (2) 30-60 years old, and (3) over 60 years old. We were able to isolate HCEC from 100% of the tissue samples from group 1 (3/3), 50% of the tissue samples from group 2 (9/18), and 31.25% of the tissue samples from group 3 (5/16) as listed in Table 2. These results showed that HCEC are more readily obtained from younger donors. Doubling times for cells from each age group were calculated after 1 month in culture (approximately passage 4-5). There were no significant differences between the doubling times calculated for cells from group 1 (≤30 years old) and group 2 (30-60 years old). However, the doubling time of group 3 (>60) was longer than those calculated for the other groups (P<0.05).

TABLE 2

Number of success of corneal endothelial cell isolation and doubling time of cells.

| | n | No. of success | Days from cornea collection to cell processing | Doubling time (hr) |
|---|---|---|---|---|
| Donors ≤ 30 years old | 3 | 3 | 9 ± 4.6 | 22.8 ± 3.6 |
| 30 < Donors ≤ 60 | 18 | 9 | 7.6 ± 1.5 | 23.5 ± 2.3 |
| 60 < Donors | 16 | 5 | 6.4 ± 2.8 | 39.6 ± 12.8 |

Example 3

Seeding the Decellularized Corneal Scaffolds

Approximately 30,000 CECs were seeded on the decellularized scaffold (8 mm diameter). Acellular corneas were placed in the bottom of a well of a 48-well dish, and the cell suspension was layered on top, allowing the seeding to take place by simple gravitational settling.

The construct was placed in EGM-2 media (Lonza, Walkersville, Md.) supplemented with fetal bovine serum (to a final concentration of 10%) for seven days, and then analyzed.

Scanning electron microscopy (SEM) was performed on fresh (frozen) samples to determine CEC coverage of the stroma. Isolated hCEC formed confluent monolayers with a phenotype typical of endothelial/epithelial cells (FIGS. 2, A&B). The decellularization process efficiently removed each of the stromal, epical and basal cell layers (FIG. 1). When seeded on the surface of decellularized corneas, hCEC formed a single cell monolayer, similar to native cornea (FIG. 1, right upper and lower panels).

In addition, cross sections were stained with H&E, DAPI, and ZO-1. FIG. 1 depicts both a DAPI stained construct (C) and a ZO-1 stained section (H&E counter stained). Results indicated that, after two weeks in culture, the seeded CECs form a confluent monolayer on the corneal stroma and express ZO-1, which is a maker of tight junction formation. The cells expressed markers consistent with CECs (AE1/AE3, Connexin-43, Zo-1 (FIG. 2, C), VE-Cadherin and vWF) but not CD-31. The cells also expressed Na+/K+ ATPase.

Figure 6:
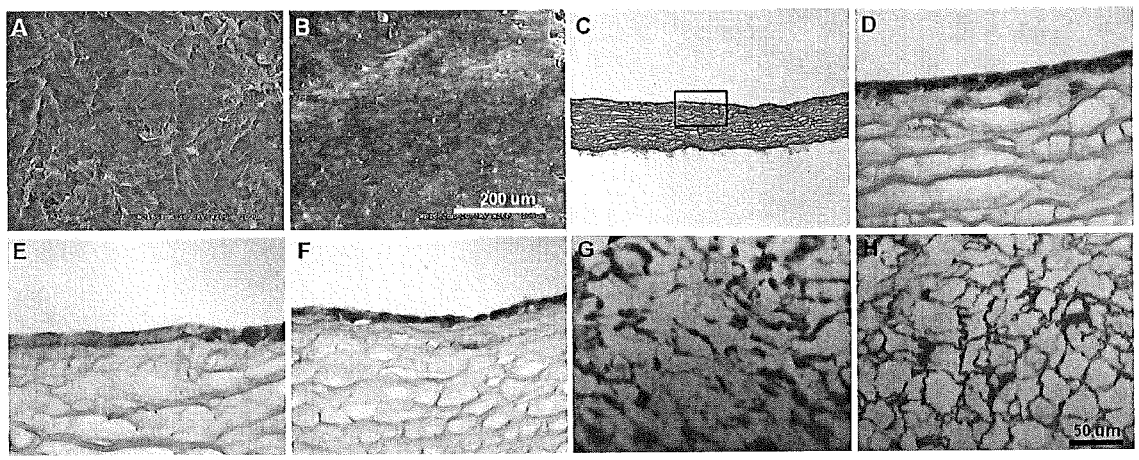
FIG. 6. SEM images of HCEC seeded decelluarized corneal human stromas; (A) unseeded and (B) HCEC-seeded (magnification, ×200), Cross sections of HCEC-seeded decelluarized stromas were stained with (C) H&E (magnification, ×100), immunohistochemistry for (D) ZO-1, (E) connexin 43, and (F) Na+/K+ ATPase (magnification, ×630), and (G,H) Alizarin Red (magnification, ×400); (G) 130 cells/mm$^2$ and 3000 cells/mm$^2$ of cell seeding density.

Staining revealed extensive cell coverage of the corneal stroma whether cells were seeded at 130 cells/mm$^2$, or 3000 cells/mm$^2$ (FIG. 6) These results confirmed that functional HCEC could be maintained on the decellularized stromas in vitro.

In summary, human corneal endothelial cells were isolated from cadaveric donor tissue and formed a typical monolayer when seeded on the surface of decellularized cornea.

Example 4

Mechanical Testing

To examine the effects of the decellularization process on the mechanical properties of the corneal stromas, we examined the response of decellularized human corneal stromas to mechanical loading. Analyses of the tensile properties of corneal tissues were performed on both decellularized corneas and native corneas using uniaxial load testing equipment (Model #5544, Instron Corporation, Issaquah, Wash., USA). A segment of cornea (3.9 mm of width, 8.7 mm of length, and 0.13-0.2 mm of thickness) was clamped at its cut ends for axial testing (n=3). The crosshead speed was set at 0.6 mm/min and the test was stopped when the load decreased by 10% after the onset of failure.

Figure 5:
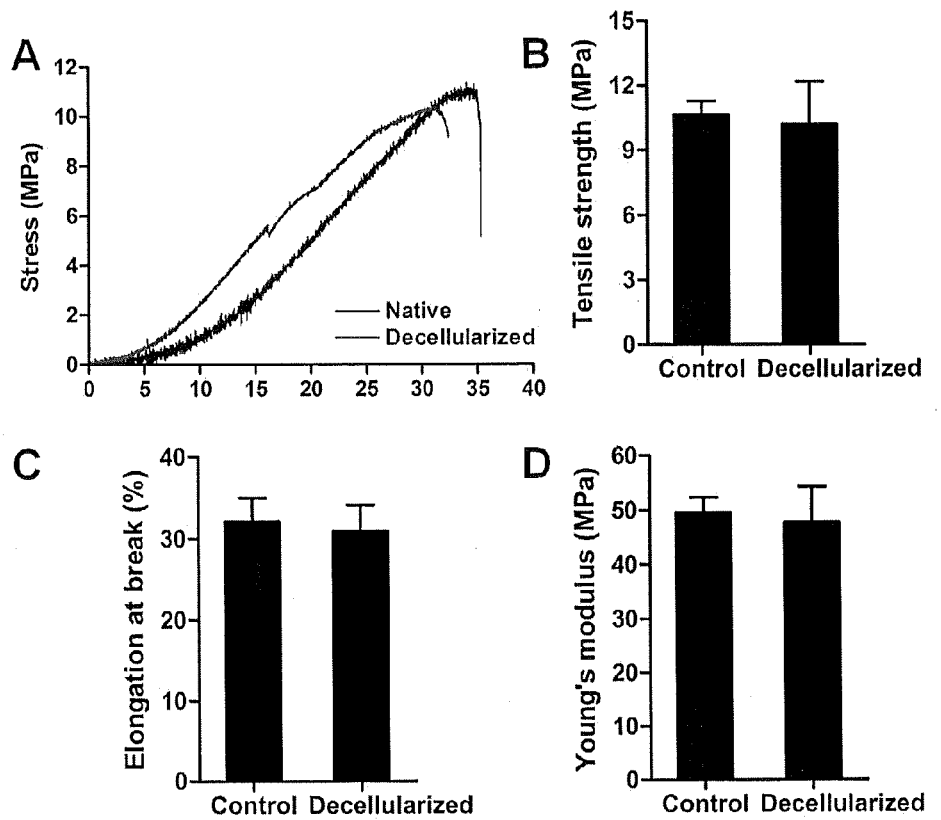
FIG. 5. Mechanical properties of native human corneal stroma and decellurized corneal stromas; (A) stress-strain curve, (B) tensile strength, (C) elongation at break, and (D) Young's modulus. Mechanical properties of decelluarized stromas were tested using mechanical tester. A comparison between native corneal stroma and decelluarized stromas showed similar mechanical behavior.

A comparison between native corneal stromas and decellularized stromas showed similar mechanical behavior (FIG. 5A). The ultimate tensile strength of native corneal stromas was 10.6±0.7 for the native corneal stromas and 10.2±2.0 MPa for decellularized stromas (FIG. 5B). Additionally, the decellularization process had no significant effects on elongation at break (32.0±3.0% for native stromas and 30.8±3.3% for decellularized stromas, FIG. 5C) and Young's modulus (49.5±2.8 MPa for native stromas and 47.6±6.7 MPa for decellularized stromas, FIG. 5D). These results indicate that the decellularization of human corneal stromas reliably removes cellular components from these tissues while preserving both the ECM architecture and adequate mechanical properties.

Thin-sliced decellularized human corneal scaffolds retain the biomechanical properties of the native corneas, thereby providing a construct that may be more easily applied to the posterior surface of the cornea during transplantation surgeries.

Example 5

In vivo testing. Endothelialized acellular corneas were prepared and transplanted into rabbits (n=3). Sectioned explants harvested after 3 or 4 weeks show an intact bioengineered cornea with H&E, alzarin red and trypan blue staining, and also express Na$^+$/K$^-$, ZO-1 and connexin-43 (data not shown).

The foregoing is illustrative of the present invention, and is not to be construed as limiting thereof. The invention is defined by the following claims, with equivalents of the claims to be included therein.

That which is claimed is:

1. A method of making an endothelial scaffold, comprising the steps of:
providing a sectioned corneal stroma, said stroma having a thickness of between 50 and 200 micrometers, wherein said providing comprises sectioning a cornea parallel to the endothelial surface thereof;
decellularizing said stroma to form a scaffold, wherein said decellularizing comprises treating said stroma with a detergent and/or basic solution, or comprises treating said stroma with a hypo-osmotic solution; and
seeding cultured endothelial cells onto said scaffold to form an endothelial scaffold,
wherein said cultured endothelial cells are corneal endothelial cells, and wherein said cultured corneal endothelial cells are positive for the markers: Zona occludin-1 (ZO-1), Na+/K+ ATPase, connexin-43, cytokeratin AE1/AE3, von Willebrand factor (vWF), and VE-Cadherin; and are negative for the marker CD31,
to thereby produce said endothelial scaffold.

2. The method of claim 1, wherein said cultured endothelial cells form a monolayer of hexagonally-shaped cells on said scaffold.

3. The method of claim 1, wherein said cells have been passaged between 1 and 20 times.

4. The method of claim 1, wherein said cornea is a human cornea.

5. The method of claim 1, wherein said endothelial cells are human endothelial cells.

6. The method of claim 1, wherein said sectioned corneal stroma has an average thickness of between 75 and 150 micrometers.

7. The method of claim 1, wherein said sectioned corneal stroma has an average thickness of between 100 and 130 micrometers.

8. The method of claim 1, wherein said sectioning is carried out with a microtome.

9. The method of claim 1, wherein said decellularizing comprises treating said stroma with a hypo-osmotic solution.

10. The method of claim 1, wherein said decellularizing comprises treating said stroma with a detergent and/or basic solution.

* * * * *